United States Patent [19]

Tanaka

[11] 4,392,829

[45] Jul. 12, 1983

[54] METAL-PORCELAIN DENTAL RESTORATION AND METHOD OF MAKING

[76] Inventor: Asami Tanaka, 9307 North Lavergne, Skokie, Ill. 60077

[21] Appl. No.: 249,682

[22] Filed: Mar. 31, 1981

[51] Int. Cl.³ ............................ A61C 5/08; A61C 5/10
[52] U.S. Cl. .................................. 433/222; 433/208; 433/223
[58] Field of Search ............... 433/222, 223, 218, 206, 433/207, 208; 264/19, 20

[56] References Cited

U.S. PATENT DOCUMENTS

| | | | |
|---|---|---|---|
| 797,515 | 8/1905 | Hughes | 433/208 |
| 1,609,549 | 12/1926 | Jaques | 433/218 |
| 1,782,552 | 11/1930 | Supplee | 433/222 |
| 1,892,490 | 12/1932 | Hejemann | 433/222 |
| 2,770,040 | 11/1956 | Moyer | 433/218 |
| 2,980,998 | 9/1961 | Coleman et al. | 433/222 |
| 3,273,242 | 9/1966 | Andrew | 433/223 |
| 4,100,678 | 7/1978 | Yatabe | 433/10 |

FOREIGN PATENT DOCUMENTS 5391 of 1905 United Kingdom ................ 433/208

OTHER PUBLICATIONS

"The Technic of Porcelain Jacket Crowns and the Relationship to Periodontia", Slocum, Dental Digest, 1924.
"Ceramic Restorations: One Bake Technique", by Asami Tanaka.
"Quintessence of Dental Technology", 7/1980, pp. 33-41.
"Full Circle in Ceramics, The Development of a New Porcelain Fused to Metal Restoration", by Hunt et al. The Compendium on Continuing Education, vol. I, No. I, Jan./Feb. 1980, Continuing Education Article #1, pp. 7-13.

*Primary Examiner*—John J. Wilson
*Attorney, Agent, or Firm*—Neuman, Williams, Anderson & Olson

[57] ABSTRACT

A baked metal-porcelain dental restoration is provided, including a method of making same. The restoration includes a substrate formed from a non-cast thin metal foil having a textured exterior surface onto which a dental porcelain jacket is directly bonded without any intermediate interface compositions. The exterior of the porcelain jacket may be configured as necessary to provide a desired occlusal surface.

The dental restoration is made by providing a support post with a configuration that corresponds to the shape of a tooth base in a patient's mouth. The support post is coated with a thin spacing layer. A thin metal foil is swaged around the coated support post to substantially conform to the shape of the post. The exterior of the foil substrate is textured and porcelain powder is applied thereto without the use of any intermediate interface composition between the foil and powder. The metal substrate and applied powder are baked to bond the porcelain directly to the metal foil. The porcelain exterior is then finished as prescribed to provide the desired occlusal relationship with other teeth.

15 Claims, 4 Drawing Figures

METAL-PORCELAIN DENTAL RESTORATION AND METHOD OF MAKING

FIELD OF THE INVENTION

This invention relates to baked metal-porcelain dental restorations using a thin metal foil substrate and to the method of making same. The substrate improves the quality of the restoration, both mechanically and aesthetically, while reducing the materials and labor necessary to fabricate the restoration.

BACKGROUND OF THE INVENTION

Over time, porcelain has gained universal acceptance as a material for dental restorations. Its color approximates natural shading, it may be contoured to form a prescribed occlusal surface, it is durable in saliva, it has reduced thermal conductivity, and it resists abrasion from food and brushing. However, porcelain has a tendency to fracture due to its crystalline structure.

The ability of porcelain to resist fractures has been greatly enhanced by chemically bonding or fusing the porcelain to a metal substrate with the assistance of a suitable interface composition. Although the metal adds strength, it is the chemical bond that inhibits fracture of the porcelain and significantly enhances its strength and suitability in dental applications.

The prior art includes, in the more distant past, a porcelain jacket crown. In its final form it does not utilize a metal foil substrate. However, when constructing a porcelain jacket crown, a metal foil substrate, such as platinum, provided a support post to which porcelain was applied. Platinum was used because it did not adhere to the porcelain and could be easily removed when the crown was complete and ready for use. Such a crown was susceptible to fractures.

The next type of metal-porcelain restoration utilized a cast metal substrate that was typically 0.2 to 0.3 mm. thick and comprised of gold and non-gold alloys. Porcelain was bonded to the cast metal by baking, with the assistance of a suitable interface composition, and the combined metal-porcelain restoration was then fitted to the patient's mouth. The casting process was costly because of the necessary precious materials and time required, and it demanded a high degree of skill in casting techniques. In addition, the fit was often less than desireable and an unsightly metal margin was readily apparent.

In the more recent past, metal-porcelain restorations have been made with a swaged metal foil substrate. These restorations eliminated the need for metal castings and their attendant disadvantages, and permitted one to easily and quickly learn the techniques of swaging the foil around a die. This expedited the manufacturing process, and eliminated the use of gold alloys and time-consuming castings, thereby reducing costs. In addition, the reduction in metal thickness to approximately 25 microns allowed for less reduction of the tooth base and permitted the use of porcelains that were more suitable than those used with cast metal.

However, as with cast metal substrates, the porcelain was not bonded directly to the metal foil. Instead, a series of intermediate steps was undertaken to create an interface between the metal foil and porcelain. These intermediate steps required that a thin layer of tin be electrodeposited on the foil substrate. The tin coated substrate was then baked to oxidize the tin and provide a suitable substrate for bonding. Thus, the porcelain was not bonded directly to the swaged metal foil substrate. Absent the tin-oxide coating, the porcelain would not bond to the substrate.

In addition to the aforementioned steps and materials necessary to create the tin-oxide interface, this prior art interface coating is excessively dark, necessitating the application and baking of one or more opaque porcelain layers so that the restoration would be aesthetically acceptable. Once these additional steps were completed, body or dentin porcelain was applied over the opaque layers, followed by enamel outer porcelain. Thus, the tin coating and subsequent oxidation required additional fabrication time and equipment, subsequent color correction, and additional baking steps for both oxidation and applying an opaque porcelain underlayer.

The first foil substrate metal-porcelain restorations used two platinum foils. One foil was a permanent part of the restoration and the second foil was used only during fabrication. The one foil was tin plated, oxidized, coated with an opaque layer, baked, and eventually bonded to the porcelain so as to extend close to but not beyond the margin of the tooth. The second foil was sandwiched between the first foil and the die or tooth base and was not tin plated. It extended below the margin of the tooth and served as a removeable matrix for the marginal region where there was no inner tin oxide coated foil. When removed, it provided a space for adhesive. The porcelain bonded to the tin-oxide coated one foil but not to the uncoated second foil. Once the bonding process was complete, the inner (second) foil was removed and the restoration was fixed in a patient's mouth. This process resulted in a restoration with a metal-porcelain crown portion and a margin of pure porcelain without a metal substrate. This eliminated an unsightly metallic margin, but the problems associated with the dark tin oxide layer and unnatural appearance persisted. In addition, because of the removal of the foil matrix at the margin, twin foil restorations suffered from two additional problems. One concerned the form that the porcelain would take when it abutted to a foil that it did not adhere to, and the second concerned an increased frequency of cement washout at the margin of the restoration.

Metal-porcelain restorations having single layer foil substrates were subsequently developed, but they still required tin-plating, oxidation, the application of opaque material, and additional baking, along with the extra time, materials, and skills required to complete these steps. Moreover, these restorations still suffered from all of the aesthetic drawbacks associated with the dark tin-oxide layer underneath the dental porcelain.

SUMMARY OF THE INVENTION

It is an object of the present invention to provide a metal-porcelain dental restoration that overcomes the aesthetic and mechanical shortcomings of the prior art, provides improved dental restorations, and simplifies and shortens the fabrication process.

It is a further object of the present invention to provide a metal-porcelain restoration having a non-cast thin metal textured foil substrate with porcelain bonded directly thereto without the use of any intermediate interface composition.

It is a further object of the present invention to provide a method of making a metal-porcelain restoration with porcelain bonded directly to a non-cast thin metal foil substrate, thereby eliminating the need to apply or create any interface compositions between said metal foil and porcelain.

The present invention overcomes the shortcomings of the prior art by providing a baked metal-porcelain dental restoration having a non-cast thin metal foil substrate. One surface of the foil is textured and is capable of bonding directly to dental porcelain when baked without any intermediate interface compositions. A porcelain layer is bonded directly to said textured surface, and the exterior of the porcelain may be configured as prescribed. The restoration is made by first providing a support post or die. The post is coated with a thin spacing layer. A thin metal foil is swaged around the coated post to form a substrate having a cup-like configuration. The exterior surface of the substrate, or that portion to which porcelain is to be bonded, is textured and then porcelain powder is applied directly thereto without any interface compositions therebetween. The metal and porcelain is baked to bond the porcelain directly to the foil, and then the restoration may be finished to provide the desired occlusal relationship with other teeth.

DESCRIPTION

The following detailed description is illustrative of the best mode presently known for carrying out the invention, and is not to be interpreted as limiting the disclosure.

Figure 1:
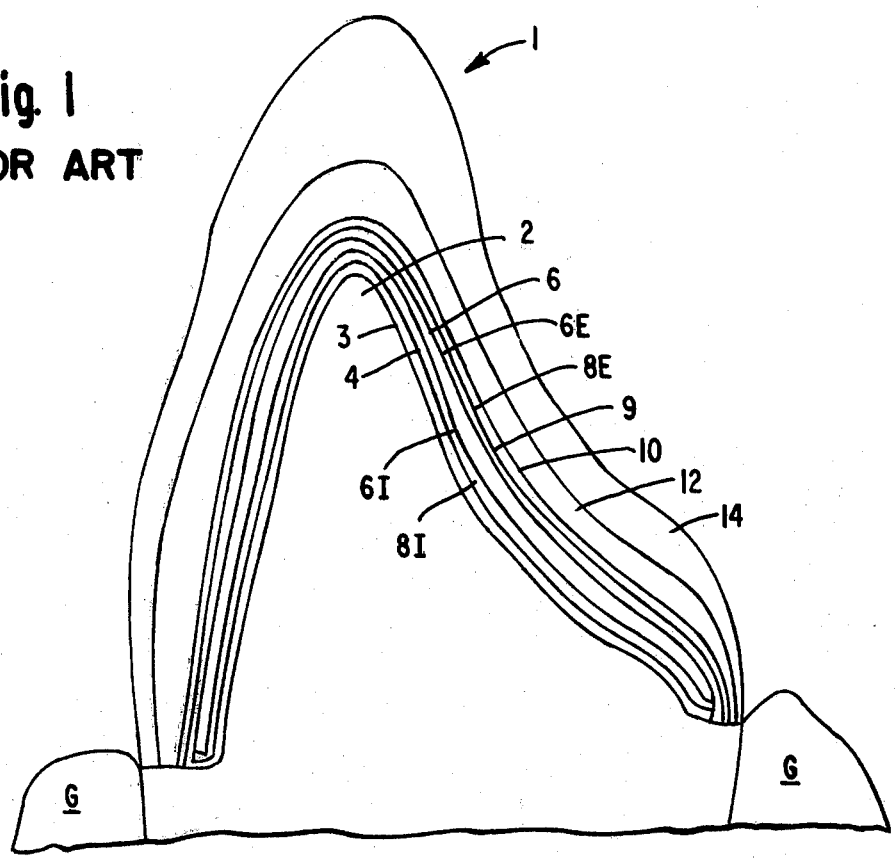
FIG. 1 is an enlarged fragmentary vertical cross sectional view of a single foil baked metal-porcelain dental restoration according to the prior art and shown positioned within the patient's mouth.

FIG. 1 is a typical prior art baked metal-porcelain dental restoration having a single thin metal foil substrate. The entire restoration 1 is supported and held in position by a tooth base 2, which is a portion of the patient's jaw and not a portion of the restoration. The base is created from an existing tooth by grinding away the exterior to provide a suitably shaped projection for anchoring the restoration thereto. The patient's gum tissue G is adjacent the post. The restoration 1 is secured to the base 2 using conventional techniques, such as gluing with a carboxylate or glass ionomer cement 3. It is common when making the restoration to make a die of the base 2, using conventional techniques. The die is used to configure the inside of the restoration and insure a proper fit, in a manner to be described hereinafter, without the necessity of having the patient present for each step of the fabricating process.

The conventional restoration normally comprises a substrate 6 of one (or more) layer of platinum foil. A single layer is generally preferred. The thin metal foil, once shaped to obtain an interior configuration that corresponds to the exterior of the base 2, has a thin layer of tin electrodeposited on its exterior surface 6E and interior surface 6I. The tin coated substrate is subsequently baked a first time to form exterior and interior layers of tin oxide 8E and 8I, respectively. The tin oxide layers alloy to the surface of the metal foil at their common surface and form suitable interface compositions for bonding with porcelain and improving adhesion of the cement between the restoration 1 and tooth base 2.

The tin oxide that comprises the interface composition is normally a very dark color. This is undesireable because, despite the application of translucent porcelain, the ultimate restoration will have a dark, unnatural and unsightly color. Thus, to avoid this problem it was necessary to apply one or more layers of opaque porcelain 10 to the exterior 6E of the foil substrate. This application, in turn, necessitated one or more subsequent bakings to cure the opaque coating prior to applying the dentin porcelain 12 and enamel porcelain 14 that form the main portion of the restoration. The opaque porcelain 10 fuses to the tin oxide layer 8E at their common surface 9. The restoration is now suitable for the application and baking of body or dentin porcelain 12 and enamel porcelain 14, which may be done according to conventional techniques. The restoration may then be finished as desired to provide the proper color and occlusal surface, although accurate and natural coloration is difficult to obtain due to spectral reflection from the opaque layers masking the tin oxide.

Figure 2:
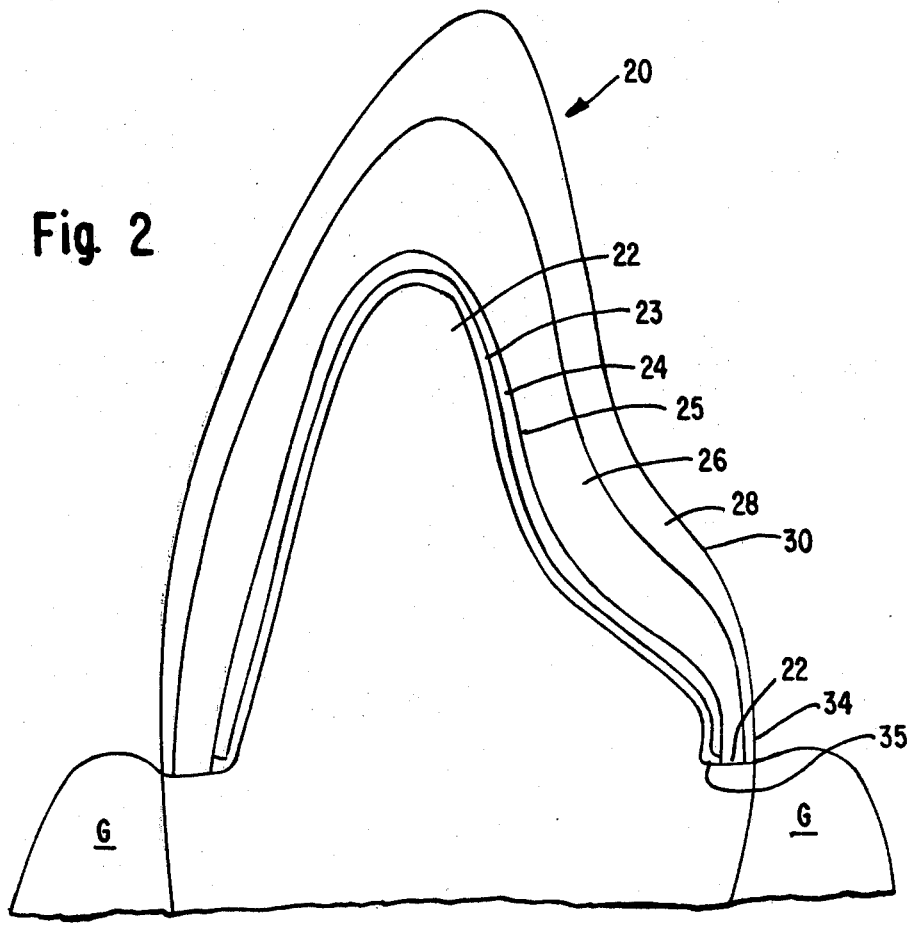
FIG. 2 is similar to FIG. 1 but showing a baked metal-porcelain dental restoration according to the present invention.

FIG. 2 shows an embodiment of the improved baked metal-porcelain dental restoration 20 supported and held in position by a tooth base 22, which as previously mentioned is a portion of the patient's jaw and is surrounded by the gum tissue G. Restoration 20 is secured to the base 22 using conventional techniques, such as a suitable glue or adhesive 23 at the interface between the base 22 and the restoration 20.

Restoration 20 includes a substrate 24 of a non-cast thin metal foil and swaged thin metal cap of soft non-precious alloys and precious alloys, such as platinum, nickel-gold, paladium-gold, or platinum alloys (e.g. platinum-iron and platinum-tin). The thickness of the foil is approximately 25 or more microns. Although not necessary, it is also desireable to select a foil having a coefficient of thermal expansion that closely matches the coefficient of thermal expansion for porcelain thereby minimizing undesireable effects during baking.

The metal foil 24 has its outer surface 25 textured by sandblasting or the like, which results in the subsequently applied porcelain bonding directly to the foil. There are no interface compositions, such as tin plating or tin oxide coating between the metal foil and porcelain as was common in the past to insure bonding of the metal and porcelain. In fact, in prior practice platinum was frequently used to avoid bonding between the foil and porcelain. In the improved restoration 20 the bond between the foil and porcelain is not an adhesive bond; but, instead the two surfaces react to chemically bond together and thereby enhance the strength of the porcelain.

As noted hereinafter, body or dentin porcelain 26 is applied directly to the textured exterior surface of the metal foil 24. Enamel porcelain 28 is subsequently applied directly over the dentin porcelain and forms the exposed outer surface 30 of the restoration which may be colored to make it aesthetically pleasing and configured to provide the desired occlusal relationships with other teeth. This may be done in any manner well known in the art.

The margin or end 34 of the restoration adjacent the patient's gum tissue G may, if desired, have a small portion of the foil substrate 24 removed from around the entire interior periphery thereof so as to create a channel 35 for excess adhesive. The channel eliminates any aesthetically undesireable metal being exposed at the margin of the restoration.

Figure 3:
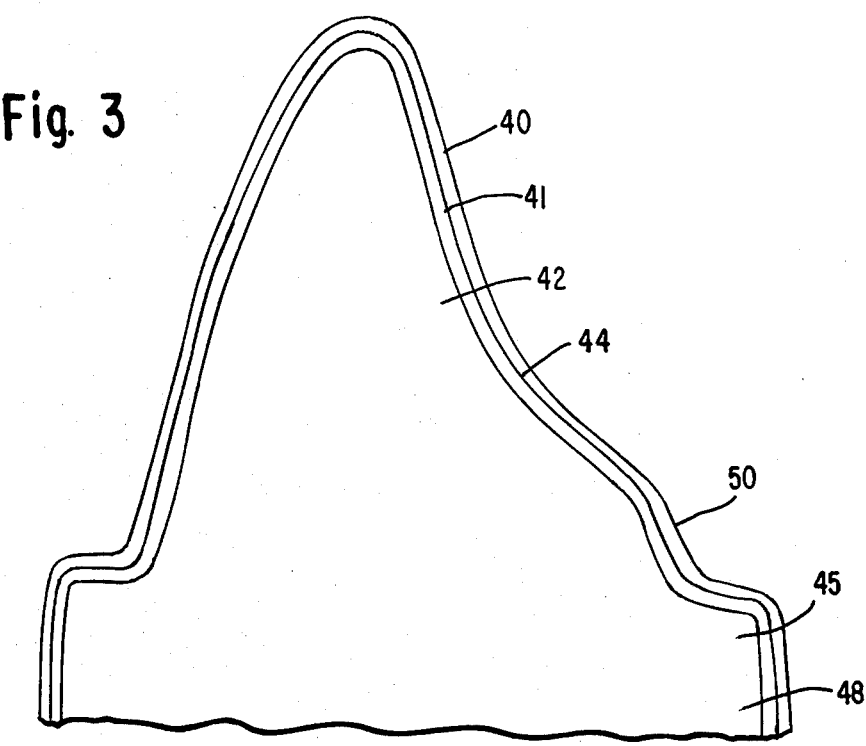
FIG. 3 is similar to FIG. 2, but showing only a coated support post with a non-cast thin metal foil swaged thereabout.

Referring to FIG. 3, the metal-porcelain restoration 20 is fabricated by utilizing a separate support post 42 having a configuration capable of supporting and holding in position a dental restoration. Post 42 is usually a replica created from an existing tooth in which the exterior thereof has been ground to provide a suitably shaped base 22. The post 42 has a shoulder 45 which coincides with a shoulder 22' formed in the base 22 at about the gum line. Normally, there is one post for each tooth, but this may be varied as necessary. The post replica is made using techniques well known in the art and includes a portion 48 which depends from the shoulder 45.

A spacer coating 41 (e.g. a lacquer, arcylic liquid, or rubber) is applied by spraying or brush to the entire support post. The coating has a relatively uniform thickness of about 50 microns and does not become a part of the finished restoration. As will be described hereinafter, coating 41 provides a space between a thin metal foil 40 and post 42 thereby insuring that the interior configuration of the restoration will match the exterior configuration of the tooth base 22.

The non-cast thin metal foil 40 is formed into a substrate for the dental restoration by swaging it around the coated post 42. The swaging may be done manually by a dental technician in a matter of minutes. The substrate has a generally cup-like interior configuration 44 conforming substantially to the exterior configuration of the coated post 42 and an exterior configuration determined by the swaging. For convenience, any excess foil 46 is pressed down so as to encompass the lower portion 48 of the replica.

Once the metal foil has been swaged, its exterior surface 50 is textured, preferably by sandblasting, but may be accomplished with other abrasives such as a diamond point or bar. The texturing results in direct bonding of the porcelain to the exterior surface of the foil substrate without the use of intermediate interface compositions, such as tin-oxide. In addition, the texturing provides a larger surface area on which to bond the porcelain, enhances mechanical bonding, improves adhesion, assists the initial attachment of the ceramic powder to the exterior surface of the metal foil while baking, and helps to eliminate cracks normally caused by porcelain shifting on the substrate surface.

Figure 4:
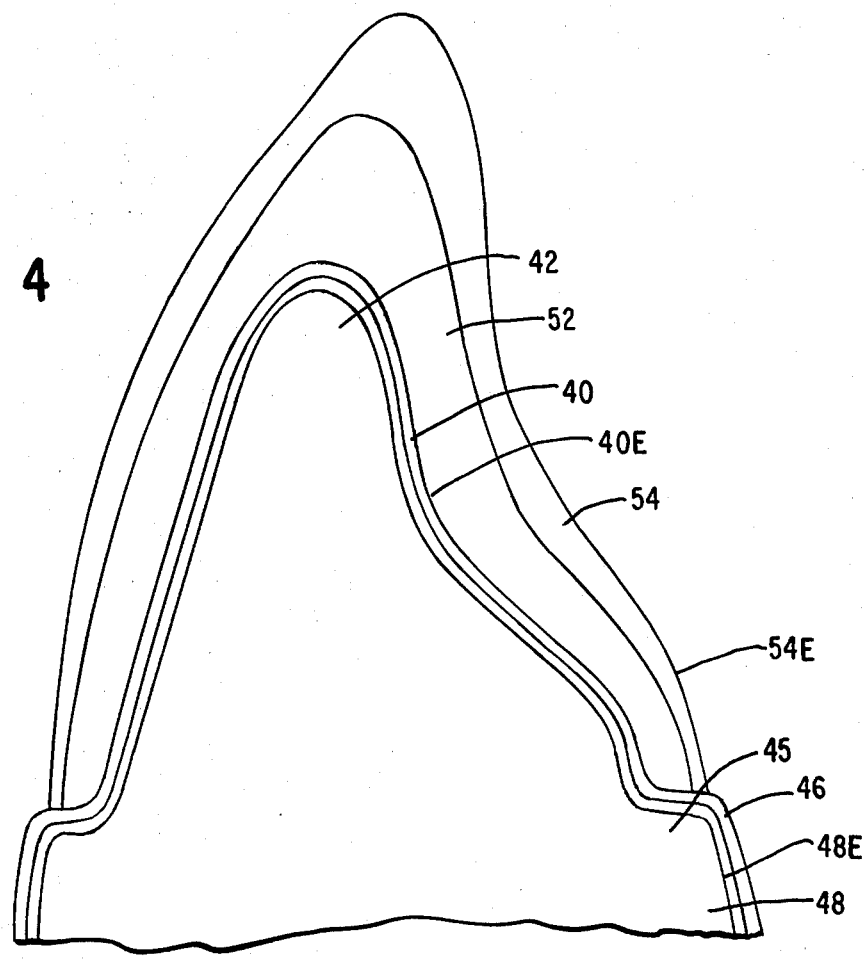
FIG. 4 is similar FIG. 3 but showing dentin and enamel porcelain applied to the exterior of the swaged metal foil substrate.

Referring to FIG. 4, a commercially available body or properly colored opaquish dentin porcelain 52 is applied directly to the exterior surface 40E of the metal foil 40. Depending upon one's preferred technique, enamel porcelain 54 may also be applied at this time to the exterior of porcelain 52. Porcelain 54 should approximate as closely as possible the desired tooth anatomy with the exterior 54E thereof aligned with the exterior 48E of the support portion 48. The porcelain 52, 54 extends down to shoulder 45 which corresponds to the location of the shoulder 22' of the tooth base 22. The metal foil substrate with the applied powders of porcelain 52, 54 is then baked at sufficiently high temperatures (approximately 950° C.) to bond the porcelain powder 52 directly to the metal foil.

There are no platings, oxides, or other interface compounds applied between the metal foil and the porcelain to effect bonding therebetween, as taught in the prior art. Thus, several steps are omitted, saving fabrication time, materials and energy necessary to complete those steps. All of these savings make the process less expensive, yet result in an improved restoration. Also, because the dark undesireable tin oxide layer is omitted, the required opaque layers are not required enabling better shading and color matches to be obtained, often in less time.

After baking, the restoration may be finished by shaping the porcelain exterior to the prescribed occlusal relationship with adjacent and opposing teeth; coloring the porcelain exterior as needed or desired; and removing any excess metal foil 46 which extends below the margin 34 of the enamel porcelain 54. Unless removed the excess foil might be visible when the restoration was positioned in a patient's mouth. As necessary or desireable, and before the restoration is mounted on the base 22, a small marginal portion of the foil substrate may be removed so as to form the channel 35. This is facilitated by leaving the marginal portion of the foil substrate untextured, whereby porcelain will not bond thereto.

Obviously, many modifications and other embodiments for the subject invention will come to one skilled in the art having the benefit of the foregoing teachings, including the drawings. Therefore, the invention is not to be limited thereto and any modifications are intended to be included within the scope of the appended claims.

What is claimed is:

1. A baked metal-porcelain dental restoration for mounting on a patient's shaped tooth base said restoration comprising:
    (a) an interior substrate of non-cast semi-precious alloy of soft, swageable thin metal foil for mounting on the shaped tooth base, said substrate having a textured exterior surface substantially free from surface coatings and an interior surface configuration that conforms substantially to the exterior configuration of said tooth base; and
    (b) a body porcelain layer chemically bonded directly to the substrate textured exterior surface without any intermediate interface composition therebetween, said porcelain layer having an exterior of prescribed configuration to provide a desired occlusal surface.

2. The dental restoration of claim 1 wherein the exterior of said substrate is substantially free from tin plating.

3. The dental restoration of claim 1 wherein said substrate comprises a single layer of metal foil.

4. The dental restoration of claim 1 wherein the thickness of the substrate is above 25 microns.

5. The dental restoration of claim 1 wherein the coefficient of heat expansion of said substrate and said porcelain layer are substantially the same.

6. The dental restoration of claim 1 wherein said substrate has a generally cup-like interior surface configuration.

7. The dental restoration of claim 1 wherein the porcelain layer comprises a predetermined number of layers of dental porcelain.

8. The dental restoration of claim 1 wherein said porcelain layer extends slightly beyond the exposed edge of said metal foil substrate and coacts therewith to form a concealed channel when said restoration is mounted on the patient's shaped tooth base.

9. A method of making a baked metal-porcelain dental restoration having a substrate of swageable thin metal foil and a porcelain layer bonded directly to the exterior of said metal foil, comprising:

(a) providing a support post having a configuration capable of supporting a dental restoration;

(b) coating the exterior of said support post with a thin spacing layer;

(c) swaging a non-cast semi-precious alloy of soft thin metal foil around said coated post to form a substrate, said substrate having an exterior substantially free from surface coatings, and having an interior surface configuration conforming substantially to the exterior surface configuration of said support post;

(d) texturing a predetermined portion of the exterior surface of said substrate;

(e) applying body porcelain powder directly to the textured exterior surface portion of said substrate without the use of any intermediate interface composition;

(f) baking said substrate and said applied porcelain powder to fuse and chemically bond said powder directly to said textured exterior surface portion to form a porcelain layer; and (g) finishing the exterior of said porcelain layer.

10. The method of claim 9 wherein the configuration of said support post is a substantial replica of a corresponding tooth base formed in a patient's mouth to anchor a dental restoration.

11. The method of claim 10 wherein said finishing of said metal-porcelain restoration comprises:

(a) contouring the exterior surface of said porcelain layer to a prescribed occlusal configuration;

(b) applying predetermined coloring to the exterior of said porcelain layer; and (c) removing any metal foil substrate portion visible when said restoration is anchored to the tooth base in a patient's mouth.

12. The method of claim 9 wherein the thickness of said spacing layer is approximately 50 microns.

13. The method of claim 9 wherein said metal foil substrate is textured over substantially the entire exterior surface thereof.

14. The method of claim 9 wherein said metal foil substrate is manually swaged about the exterior of the support post.

15. The method of claim 9 wherein said substrate is textured by sandblasting.

* * * * *